United States Patent [19]

Saleh et al.

[11] Patent Number: 4,814,317

[45] Date of Patent: Mar. 21, 1989

[54] PROCESS FOR PREPARING CATALYSTS FOR PREPARATION OF AROMATIC CARBOXYLIC ANHYDRIDES

[75] Inventors: Ramzi Y. Saleh, Baton Rouge, La.; Israel E. Wachs, Bridgewater, N.J.

[73] Assignee: Exxon Chemical Patents Inc., Linden, N.J.

[21] Appl. No.: 102,164

[22] Filed: Sep. 29, 1987

Related U.S. Application Data

[62] Division of Ser. No. 782,966, Oct. 2, 1985, Pat. No. 4,728,744.

[51] Int. Cl.$^4$ .................. B01J 21/06; B01J 23/22
[52] U.S. Cl. .................................... 502/350
[58] Field of Search ........................ 502/350

[56] References Cited

U.S. PATENT DOCUMENTS

| | | | |
|---|---|---|---|
| 3,494,930 | 2/1970 | Dupevre et al. | 260/294.7 |
| 3,509,179 | 4/1970 | Friedrichsen et al. | 260/346.4 |
| 3,721,683 | 3/1973 | Yokoyama | 260/346.4 |
| 3,894,971 | 7/1975 | Reuter et al. | 252/437 |
| 3,909,457 | 9/1975 | Friedrichsen et al. | 252/476 |
| 3,926,846 | 12/1975 | Ono et al. | 252/435 |
| 4,305,843 | 12/1981 | Krabetz et al. | 252/432 |
| 4,582,911 | 4/1986 | Wachs et al. | 549/248 X |
| 4,582,912 | 4/1986 | Saleh et al. | 549/248 X |

FOREIGN PATENT DOCUMENTS

| | | |
|---|---|---|
| 1140264 | 1/1969 | United Kingdom . |
| 1237954 | 7/1971 | United Kingdom . |

OTHER PUBLICATIONS

S. Matsuda et al., "Titanium Oxide Based Catalysts—A Review", Applied Catalysis, 8 (1983), 149–165.

R. J. H. Clark, Chapter 9, "Oxides, Sulphides and Other Binary Compounds", *The Chemistry of Titanium and Vanadium* (1968), 266–291.

F. Roozeboom et al., "Vanadium Oxide Monolayer Catalysts", American Chemical Society, *J. of Phys. Chem.*, vol. 84, No. 21 (1980), 2783–2791.

S. Brunauer et al., "Adsorption of Gases in Multimolecular Layers", Feb., 1983, 309–319.

*Primary Examiner*—W. J. Shine
*Attorney, Agent, or Firm*—D. E. Furman

[57] ABSTRACT

In accordance with the process of this invention, an improved catalyst for molecular oxidation of an aromatic hydrocarbon to form the corresponding aromatic carboxylic anhydrides is prepared by the steps of forming a catalyst precursor by depositing on titanium dioxide solids in the anatase form a continuous monolayer amount of at least one source of zirconium dioxide, calcining the thus-formed catalyst precursor under conditions sufficient to convert the zirconium oxide source into the oxide form, depositing upon the calcined catalyst precursor a catalytically effective amount of at least one vanadium compound which is convertible into vanadium oxide upon heating and calcining the vanadium-deposited solids under conditions sufficient to convert the vanadium compound into vanadium oxide.

10 Claims, 2 Drawing Sheets

PROCESS FOR PREPARING CATALYSTS FOR PREPARATION OF AROMATIC CARBOXYLIC ANHYDRIDES

This is a division of application Ser. No. 782,966, filed 10/2/85, now U.S. Pat. No. 4,728,744.

BACKGROUND OF THE INVENTION

This invention relates generally to the manufacture of aromatic carboxylic anhydrides, and more particularly to novel catalysts and methods for their use in manufacturing phthalic anhydride by molecular oxidation of hydrocarbon feedstocks, in particular orthoxylene.

DESCRIPTION OF THE PRIOR ART

Aromatic carboxylic anhydrides are widely produced in large quantities through the molecular partial oxidation of hydrocarbon feedstocks, particularly phthalic anhydride from ortho-xylene. The phthalic anhydride product is commercially useful for reactions with alcohols, such as oxo-alcohols to form the corresponding phthalic anhydride alcohol esters, which find use as plasticizers and lubricants.

Catalysts for the above partial oxidation, in which vanadium pentoxide is deposited on titania, are known in the art, for example, as disclosed in U.S. Pat. Nos. 3,909,457, 3,926,846 and 4,305,843 and British Pat. No. 1,140,264.

In U.S. Pat. Nos. 3,494,930 (1969) and 3,509,179 (1970) to BASF, oxidation catalysts containing V and Ti are disclosed in which the active catalyst components are deposited on nonporous, inert materials, e.g., fused or sintered silicates such as zirconium silicate. The patentees also disclose that the carrier can be advantageously primed, precoated or pretreated with 0.05 to 1.5 wt % of one or more oxides of V, Mo, W, Cr, Ti or Fe, prior to coating the carrier with the patentee's active catalyst composition containing $V_2O_5$ and $TiO_2$.

British Pat. No. 1,237,954 (1971) to BASF contains a similar teaching, but includes $ZrO_2$ among the group of recited, suitable nonporous inert carrier materials which are said to be advantageously primed with from 0.05 to 5 wt % of at least one oxide of Ti, Zr V, Cr, Mo, W, Fe or Co.

U.S. Pat. No. 3,721,683 (1973) to Teijin Chemicals Ltd. discloses an o-xylene or durene oxidation catalyst prepared by calcining under certain temperatures a mixture of a V compound, a Cr compound and a promoter metal (Sn plus Sb, Ge, Sn plus In, Nb, Ta, Ga and Zr).

See also S. Matsuda et al., *Applied Catalysis*, 8 (1983) 149–165, for discussion of titanium dioxide catalysts in general.

U.S. Pat. No. 3,894,971 (1975) to BASF discloses a multi-layer supported catalyst which contains in the active material from 60 to 99 percent by weight of titanium dioxide and/or zirconium dioxide, from 1 to 40 percent by weight of vanadium pentoxide and up to 6 percent by weight of combined phosphorus, in which from 0 to 0.3 percent by weight of phosphorus is in the outer layer and more than 0.3 percent up to 6 percent of phosphorus is in the remaining catalytic material Oxides of Al, Li Nb, Sn, Sb, Hf, Cr, W, Mo and alkali and alkaline earth metals are also disclosed as being suitable in the catalytically active material. The percentage of V in the inner layer is preferably greater than in the outer layer. The catalyst is prepared by first depositing onto a support a vanadium/phosphorus compound in a slurry or paste with $TiO_2$ anatase or $ZrO_2$, followed by depositing the second vanadium/phosphorus compound layer.

SUMMARY OF THE INVENTION

In accordance with the process of this invention, an improved zirconia based catalyst for molecular oxidation of an aromatic hydrocarbon to form the corresponding aromatic carboxylic anhydrides is prepared by the steps of forming a catalyst precursor by depositing on titanium dioxide solids in the anatase form at least a continuous monolayer amount of at least one source of zirconium oxide, calcining the thus-formed catalyst precursor under conditions sufficient to convert the zirconium oxide source into the oxide form, depositing upon the calcined catalyst precursor a catalytically effective amount of at least one vanadium compound which is convertible into vanadium oxide upon heating and calcining the vanadium-deposited solids under conditions sufficient to convert the vanadium compound into vanadium oxide.

The catalysts of this invention are surprisingly superior to aromatic carboxylic anhydride catalysts comprising vanadium oxide on bulk zirconium dioxide. It has been surprisingly found that sequentially depositing the zirconium oxide source onto a $TiO_2$ anatase prior to depositing the vanadium oxide source onto the desired $ZrO_2$ base is critical in order to achieve the improved catalyst selectivity of the present invention.

DETAILED DESCRIPTION OF THE INVENTION

Figure 1:
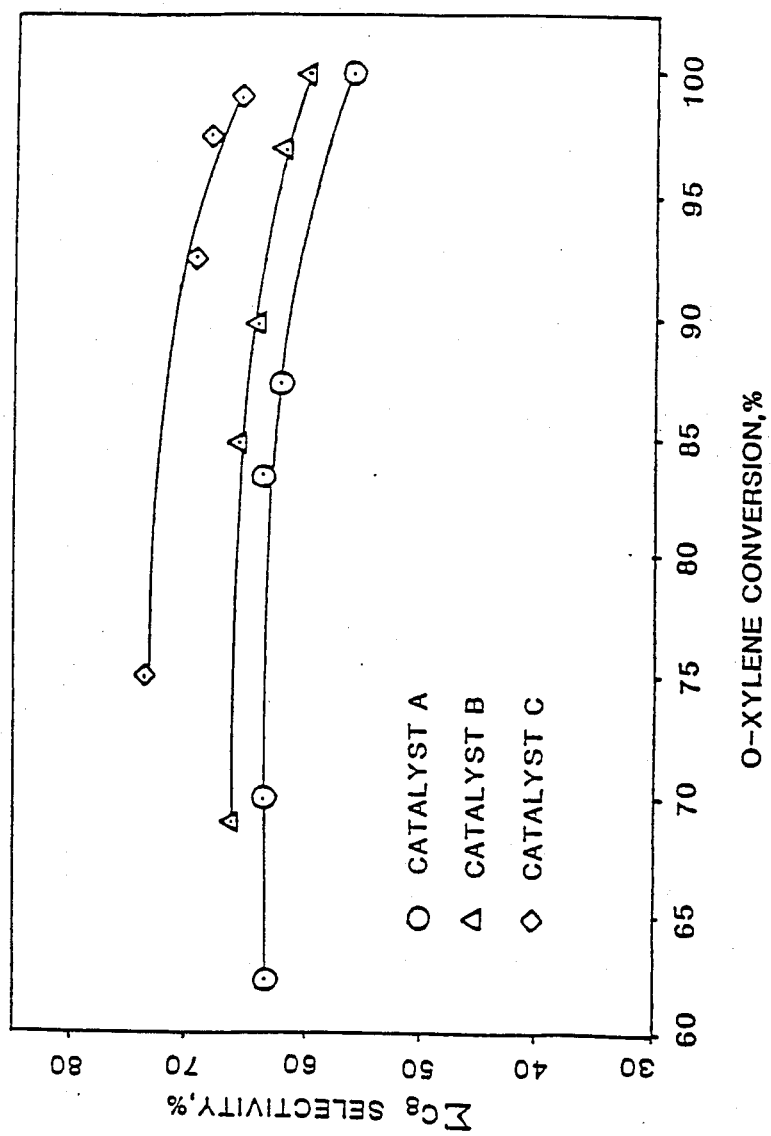
FIG. 1 is a graphical plot of the sum of C8-oxygenates selectivities versus percent conversion of o-xylene for a series of catalysts prepared and tested as described in Examples 1–2.

This invention relates to an improved process for the manufacture of aromatic carboxylic anhydrides by catalytic oxidation of aromatic hydrocarbons and relates more particularly to an improved process for producing aromatic carboxylic anhydrides such as phthalic anhydride and pyromellitic dianhydride by reacting a mixture of an oxygen-containing gas and an aromatic hydrocarbon (such as ortho-xylene or naphthalene) in vapor phase in the presence of a novel catalyst therefor.

Catalyst Preparation

The novel catalyst of this invention is prepared by a four-step procedure, in which there is first deposited on titanium dioxide in the anatase form, zirconium oxide or at least one source of zirconium oxide, followed by calcining of this catalyst precursor to form a calcined catalyst precursor. The calcined catalyst precursor is then treated in a second deposition step with the selected amount of a vanadium oxide source, and optionally catalyst promoters, followed by calcining in a separate calcining step to obtain the desired anhydride catalysts.

Suitable sources of zirconium oxide are Zr compounds which are convertible to the oxide (e.g., to the dioxide) upon heating to the calcination temperatures in the first calcination step. Suitable Zr compounds include the halides (e.g., Cl, F, Br, and I), phosphates, oxides, carbonates, sulfates, alkoxides, (e.g., $C_2$–$C_6$ alkoxides, such as ethoxide, propoxide, butoxide, pentoxide, etc.) nitrates, hydroxides, carboxylates (e.g., acetate, formate, tartrate, salicylate, and oxalate), oxyhalides and the like. Especially preferred zirconium oxide sources are the alkoxides, halides, nitrates, hydroxides and carboxylates.

The selected zirconium oxide source can be dry mixed with the titanium dioxide or deposited on the titanium dioxide from solutions or suspensions of these zirconium oxide sources, for example, using aqueous or organic solvents. Illustrative organic solvents include formamide, diethyl acetamide, ammonium thiocyanate, molten urea or an alcohol. The solutions can be sprayed upon the titanium dioxide solids (for example, in a coating drum which has been preheated to from about 150 to about 450° C.) or impregnated thereon using conventional techniques.

If wet techniques are used to deposit the Zr metal oxide source, the wetted solids can then be conveniently dried in air (or under an inert atmosphere such as nitrogen) to at least partially remove the solvent prior to calcination. Drying can be achieved by exposing the catalyst precursor to air at room temperature for a period of from about 1 to about 100 hours or by placing it in a forced hot air oven maintained at a temperature of less than about 180° C., typically between about 60° and about 150° C. for about 1 to about 16 hours. Alternatively, the precursor can be air dried at room temperature for between about 1 and about 48 hours and then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

The thus-formed catalyst precursor is then, according to the process of this invention, calcined under conditions sufficient to convert Zr oxide source into the oxide form (e.g., $ZrO_2$) and to cause the Zr oxide to be strongly attached to the surface of the titanium dioxide. Generally, a temperature of from about 100 to about 750° C. will be sufficient and temperatures of from about 300° to about 600° C. are preferred, and a time of calcination will range generally from about 0.5 to 16 hours, with a time of from about 1 to about 5 hours being preferred. The precise temperature and time of calcination will depend upon the particular Zr oxide source which has been selected for use and should be such as to avoid substantial crystal phase transformations of the $TiO_2$ anatase into another crystalline form, e.g., rutile.

The calcination can be performed, as is preferred, in air or in the presence of an $O_2$-containing gas. Although not essential, it is desirable to maintain a steady flow of the chosen atmosphere over the catalyst precursor surface during calcination. Flow rates typically will be sufficient to provide a contact time with the catalyst of about 1 to about 10, preferably from about 1 to about 5, and most preferably from about 1 to about 3 seconds. Thus, suitable flow rates or space velocities of the calcining atmosphere may be manipulated by one skilled in the art to achieve the desired contact time.

The titanium dioxide which is employed is preferably in the anatase form. Preferably at least about 25 wt % (and most preferably from about 50 to about 100 wt %) of the titanium dioxide is in the anatase form. The titanium dioxide may be prepared by any conventional technique, for example the techniques described in R. J. H. Clark, "The Chemistry of Titanium and Vanadium", p. 267 (Elsevier Publishing Co., 1968).

The titanium dioxide used in the catalyst of this invention is composed of substantially porous particles of a diameter of from about 0.4 to about 0.7 micron and is preferably of a specific surface area of from about 1 to about 25 $m^2/g$, and more preferably of from about 2 to about 10 $m^2/g$, which are essentially aggregated masses of primary particles.

The particle diameter of the primary particles can be measured by a mercury penetration-type porosimeter. When using porous titanium oxide consisting of primary particles having a particle diameter in the range of from about 0.005 to 0.05 micron, the concentration of the slurry is from about 5 to 25% by weight, preferably from about 10 to 20% by weight. When using porous titanium oxide consisting of primary particles having a particle diameter of from about 0.05 to 0.4 micron, the slurry concentration is from about 10 to 40% by weight, preferably from about 15 to 25% by weight.

Depending upon the raw ore, $TiO_2$ may include iron, zinc, aluminum, manganese, chromium, calcium, lead, silicon, etc. These incidental elements are not detrimental to the reaction if their total amount is less than about 0.5% by weight based on $TiO_2$. Therefore, the $TiO_2$ can comprise pigment grade anatase, and no special purification procedure is required.

The quantity of the zirconium oxide source which is employed is preferably an amount sufficient to provide a calcined catalyst precursor which comprises generally from about 80 to 99.5 wt % of titanium dioxide (calculated as $TiO_2$) and from about 0.05 to 20 wt % of zirconium oxides (calculated as $ZrO_2$), and preferably from about 85 to 99.9 wt. % of titanium oxide and from about 0.1 to 15 wt. % of zirconium oxides, and more preferably from about 90 to 99 wt % of titanium oxide and from about 1 to 10 wt % of zirconium oxides (calculated as $TiO_2$ and $ZrO_2$, respectively).

In accordance with one embodiment of the present invention, the Zr oxide source is contacted with the titanium dioxide solids in an amount of at least that which would provide an amount of $ZrO_2$ sufficient to provide a continuous monolayer thereof on the titanium dioxide solids, as calculated based on (1) the specific surface area of the $TiO_2$ (as conventionally determined by wet chemical analysis and BET surface area determinations), and (2) the cross-sectional area of $ZrO_2$ atoms relative to the surface density of the $TiO_2$.

The precise amount of the Zr oxide source which is required to form a continuous monolayer of $ZrO_2$ will depend on a variety of factors, such as the Zr oxide source selected (that is, the number of gram moles of Zr per gram mole of the selected Zr oxide source), the specific internal surface area of the $TiO_2$, and other factors. As used herein, a "continuous monolayer amount" of $ZrO_2$ is defined to be the amount "$M_{min}$" as determined in the following expression (I):

$$M_{min} = (G) \times (A) \times (k) \qquad (I)$$

wherein "G" is the grams of $TiO_2$ to be treated, "A" is the specific surface area in $m^2/gm$ (BET surface area) of the $TiO_2$ to be treated, "$M_{min}$" is the grams of $ZrO_2$ to be employed and "k" is the number of grams of $ZrO_2$ required to form a continuous monolayer of $ZrO_2$ on 1 gram of $TiO_2$ having a specific surface area of 1 $m^2/gm$.

For TiO$_2$ having a specific surface area of from 1 to 25 m$^2$/gm, the value "k" in the above expression is 0.001. Therefore, expression (I) reduces to:

$$M_{min} = G \times A \times 0.001 \quad (II)$$

for TiO$_2$ having a specific surface area of from 1 to 25 m$^2$/gm. As an example of the calculation, as defined herein, a "continuous monolayer amount" of ZrO$_2$ for 10 grams sample of TiO$_2$ having a specific surface area of 10 m$^2$/gm will be (10)(10)(0.001) or 0.1 gram of ZrO$_2$, and the selected Zr oxide source should be employed in an amount sufficient to provide at least 0.1 grams ($M_{min}$) of ZrO$_2$, assuming complete conversion of the Zr oxide source to ZrO$_2$ on calcination. More preferably, however, the Zr oxide source is employed as described herein for adsorption onto the TiO$_2$ in an amount sufficient to provide from about 0.005 $M_{min}$ to 200 $M_{min}$, and most preferably from about 0.01 $M_{min}$ to 40 $M_{min}$, grams of ZrO$_2$, wherein $M_{min}$ is calculated as described above. Therefore, in the preferred embodiment of this invention, the continuous ZrO$_2$ monolayer formed on the TiO$_2$ will comprise from about 0.01 to 20 wt %, and most preferably from about 0.05 to 20 wt %, of a continuous ZrO$_2$ monolayer.

Of course, not every TiO$_2$ particle need be individually treated to form thereon a continuous ZrO$_2$ monolayer, and it can be understood that at least a majority (and most usually at least 90%) of the TiO$_2$ particles will be characterized by a continuous ZrO$_2$ monolayer when the TiO$_2$ sample is treated as described herein, particularly when using solution impregnation methods.

The intermediate calcining step, in preparing the catalyst precursor, is believed to be necessary in order to cause the zirconium oxide to form the necessary bond with the TiO$_2$ surface. It is believed that the selected Zr oxide source is adsorbed (physically or both physically and chemically) onto the surface of the TiO$_2$ and that the calcining step converts the Zr oxide source to the oxide (e.g., ZrO$_2$) which is chemically adsorbed on the TiO$_2$ surface.

The resulting calcined catalyst precursor solids are then treated to deposit thereon a source of vanadium oxide, followed by calcining in a separate step. The valence of the vanadium oxide source may vary, although the pentavalent state is preferred. The source of vanadium metal oxide may be vanadium pentoxide but is preferably a vanadium compound such as an ammonium metavanadate, vanadyl sulfate, vanadyl halide (e.g., vanadyl chloride, vanadyl dichloride), vanadyl oxyhalide (e.g., vanadyl oxychloride) metavanadic acid, pyrovanatic acid, vanadium hydroxide, and vanadyl carboxylates such as formate, tartrate, salicylate and oxalate, which can then become vanadium oxide at the calcining temperature. The vanadium compounds most convenient for the catalyst preparation are V$_2$O$_5$ and vanadyl oxalate.

The selected vanadium oxide source can be deposited on the calcined catalyst precursor from solutions or suspensions of the vanadium oxide source, for example using aqueous or organic solvents. Illustrative organic solvents include formamide, diethyl/acetamide, ammonium thiocyanate, molten urea or an alcohol. The solutions can be sprayed onto the calcined catalyst precursor solids (for example in a coating drum which has been preheated to from about 150° to 450° C.) or impregnated thereon using conventional techniques.

If wet techniques are used, the wetted solids can then be dried in air or under an inert atmosphere (such as nitrogen) as described previously, conveniently at a temperature of from about 50° to 200° C., followed by calcining for activation of the catalyst at a temperature of from about 100° to 650° C., preferably about 350° to 550° C. and for about 0.5 to 16 hours, preferably about 1 to 5 hours. The precise conditions of calcining will vary depending upon the vanadium oxide source which is employed, and should be sufficient to convert the vanadium compound into the vanadium oxide. Again, the conditions of calcining should be as to avoid substantial crystal phase transformations of the TiO$_2$ anatase into another crystalline form, e.g., rutile.

The thus-prepared catalyst will contain generally from about 0.7 to 50 wt % of vanadium oxides, calculated as V$_2$O$_5$, and the mole ratio of vanadium to Zr is preferably from about 0.1:1 to 20,000:1, and preferably from about 0.5:1 to 2000:1, of gram atoms of vanadium (calculated as vanadium) per gram atom of zirconium (calculated as Zr).

The precise quantity of the selected V source which is used in the V deposition step can therefore vary but preferably should be sufficient to provide full coverage of the exposed ZrO$_2$ surface. The minimum quantity of V$_2$O$_5$ to be provided will generally correspond to the expression (III):

$$N_{min} = (G) \times (A') \times (k) \quad (III)$$

wherein "$N_{min}$" is the weight in grams of V$_2$O$_5$ to be adsorbed as described herein on the calcined catalyst precursor, "G" is the weight in grams of the calcined catalyst precursor, "A'" is the specific surface area (BET) of the calcined catalyst precursor and "k" is the number of grams of V$_2$O$_5$ required to form a continuous monolayer of V$_2$O$_5$ on 1 gram of calcined precursor having a specific surface area of 1 m$^2$/gm.

For calcined catalyst precursors having a specific surface area of from 1 to 25 m$^2$/gm, the value "k" in expression (III) is 0.0007. Therefore, expression (III) reduces to:

$$N_{min} = (G) \times (A') \times (0.0007) \quad (IV)$$

for such calcined catalyst precursors. However, since the formation of the ZrO$_2$ continuous monolayer does not significantly alter the specific surface area (A) of the TiO$_2$, expression (IV) can be further reduced to:

$$N_{min} = (G) \times (A) \times (0.0007) \quad (V)$$

wherein $N_{min}$, G and A are all as defined previously.

The grams of the selected V oxide source (calculated as its V$_2$O$_5$ equivalent weight) employed in this invention will preferably comprise at least about 1.7 $N_{min}$, and more preferably from about 2.5 $N_{min}$ to 50 $N_{min}$, (wherein $N_{min}$ is calculated as in expression (V)) in order to ensure complete coverage of the ZrO$_2$ surfaces of the calcined catalyst precursor, since it is believed that exposed ZrO$_2$ surface on the catalyst can cause over oxidation of the hydrocarbon feed and the desired partial oxidation products (e.g., phthalic anhydride) in use of the catalyst as will be described hereinafter. (Greater than about 50 $N_{min}$ can be used if desired, but generally provides no pronounced further benefit.) The presence of more than a monolayer of V$_2$O$_5$ can be observed by examining the ZrO$_2$ catalyst surface for evidence of V$_2$O$_5$ crystallites, which are believed to comprise the V$_2$O$_5$ species which forms when V$_2$O$_5$ is used in excess of the V$_2$O$_5$ monolayer amount. Such a surface examination for V$_2$O$_5$ crystallites can be conducted using Laser Raman Spectroscopy, as described in F. Roozeboom et al, *J. Phys. Chem.*, vol. 84, p. 2783, (1980).

The surface area of the activated unsupported catalyst can vary typically from about 1 to about 25 m$^2$/g.

Surface areas herein are determined by the BET method, the general procedures and theory for which are disclosed in H. Brunaur, P. Emmett, and E. Teller, *J. of Am. Chem. Soc.*, vol. 60, p. 309 (1938).

The catalyst can further comprise effective amounts of promoter metal oxides selected from the group consisting of niobium, magnesium, calcium, scandium, yttrium, lanthanium, uranium, cerium, chromium, manganese, iron, cobalt, nickel, copper, zinc, aluminum, gallium, indium, silicon, germanium, tin, bismuth, antimony, tellurium, lead, hafnium, alkali metals (Cs, Rb, K, Na, Li) and mixtures thereof.

The promoters and/or activators are readily introduced into the catalyst during deposition of vanadium on the catalyst precursor by admixture with the vanadium compounds during the heating. These promoter and activator compounds, however, should be at least partially soluble in any solvent medium used in the particular preparation in order to be best suited for combination with the vanadium components of the catalyst.

Typical compounds of zinc (illustrative of activators as a class) are metallic zinc, zinc oxide, zinc chloride, zinc bromide, zinc iodide, zinc formate, zinc nitrate or zinc acetate. Generally, phosphorus compounds are used which have as the cation an anion which is more volatile than the phosphate anion. Various compounds may be used, such as metaphosphoric acid, triphosphoric acid, pyrophosphoric acid, orthophosphoric acid, phorphorus pentoxide, phosphorus oxyiodide, ethyl phosphate, methyl phosphate, amine phosphate, phosphorus oxybromide, and the like. The alkali metal may suitably be introduced by employing alkali metal compounds such as alkali metal salts with examples being lithium acetate, lithium bromide, lithium carbonate, lithium chloride, lithium hydroxide, lithium iodide, lithium oxide, lithium sulfate, lithium orthophosphate, lithium meta-vanadate, potassium sulfate, potassium chloride, potassium hydroxide, sodium chloride, sodium hydroxide, rubidium mitrate, cesium chloride and the like. Mixtures of two or more alkali metal compounds may be used, such as a mixture of lithium hydroxide and sodium chloride or a mixture of lithium chloride and potassium chloride. The preferred alkali metal elements are lithium, sodium and potassium, and mixtures thereof, with lithium being particularly preferred. The alkali metal compound will preferably be an alkali metal compound which either has a phosphate anion as the anion, that is a compound such as lithium phosphate, or a compound which has an anion which is more volatile than the phosphate anion.

These promoter metal oxides (or metal compounds which are sources for such oxides under calcination conditions) can be geneally added to the catalyst solids by depositing on the calcined catalyst precursor with the vanadium. The amounts of such promoter metal oxides which are employed in the catalyst can vary widely and will generally comprise from about 0.05 to 20 wt % of the finally calcined catalyst, calculated as the corresponding promoter metal oxide. This will generally correspond to a vanadium oxide:atomic promoter metal oxide ratio of from 1:1 to 500:1, wherein the vanadium content is calculated as vanadium pentoxide.

The resulting finally calcined catalyst can be employed as such or deposited (as is preferred) on an inert catalyst carrier such as silicon carbide, silicon nitride, carborundum, steatite, alumina, alundum, and the like.

At some point in their preparation, the catalysts described herein preferably are formed into structures suitable for use in a reactor, although unshaped, powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax, Methocel ®, Avicel ® and graphite and the like. Extrusion or pelleting of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titania-silica. Spray dried catalysts can also be employed for fluidized bed operations.

A catalyst support, if used, provides not only the required surface for the catalyst, but gives physical strength and stability to the catalyst material. The carrier or support typically possesses a surface area of from about 0.01 to about 200 m$^2$/g, preferably from about 0.05 to about 50 m$^2$/g, and most preferably from about 0.1 to about 10 m$^2$/g. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90% by weight, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. The supports may be of a variety of shapes, the preferred shape of the supports is in the shape of cylinders or spheres.

The particles size of a supported or unsupported catalyst used in fluidized beds is quite small, usually varying from about 10 to about 200 microns.

Inert diluents such as silica may be present in the catalyst, but the combined weight of the essential active ingredients of $TiO_2$, $ZrO_2$ and $V_2O_5$ should preferably consist essentially of at least about 5 wt %, preferably at least about 15 wt %, based on the total weight of catalyst and support.

Shaping of unsupported catalyst can be conducted prior or subsequent to calcination of the V-deposited catalyst precursor. Preferably, shaping of the unsupported catalyst is conducted on the catalyst precursor prior to deposition of V thereon. The point during which shaping with supports or carriers is conducted will vary with the type of support.

Solid supports, such as silica alumina, can be added to the reaction mixture during the formation of the catalyst precursor, or the above-described active catalyst ingredients can be sequentially deposited onto the solid support.

Vapor Phase Oxidation of Hydrocarbons

The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methyl-pentene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes, which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffinic or naphthenic petroleum sources. Full boiling range naphthas (boiling within the range of about 35°–230° C.) can be used, but it is preferred to use light naphtha cuts boiling with the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and α-carboxy maleic anhydride; pseudocumene to trimetallitic anhyride; durene to pyromellitic anhydride; and o-xylene and naphthalene to phthalic anhydride.

Preparation of Phthalic Anhydride

A preferred hydrocarbon feed for the catalyst of this invention for conversion to phthalic anhydride is ortho-xylene, or an aromatic feedstream comprising a predominant amount ortho-xylene and more preferably at least 10 mol. % ortho-xylene. In the following discussion and exemplification, therefore, ortho-xylene is used in most examples to demonstrate (but not to limit) the use of catalysts made by the process of this invention for producing phthalic hydride. (It will be understood, for example, that naphthalene can also be employed as a hydrocarbon feed to prepare phthalic anhydride).

The oxidation of ortho-xylene to phthalic anhydride may be accomplished by contacting ortho-xylene in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed. The molecular oxygen-containing gas feed (e.g., air) is preferably preheated (e.g., to from 100° to 300° C.) before introducing it into the reactor.

The gaseous feedstream to the oxidation reactors normally will contain air and typically from about 0.5 to about 10, preferably from about 1 to about 8, and most preferably from about 1.2 to about 5 mol. % ortho-xylene. About 1.0 to about 1.9 mol. % of the ortho-xylene in air is satisfactory for optimum yield of product for the process of this invention using a fixed bed reactor, and from about 2.5 to 4.0 mol. % ortho-xylene using a fluidized bed. Although higher concentrations may be employed, explosive hazards may be encountered. Lower concentrations of ortho-xylene less than about 1%, of course, will reduce the production rate obtained at equivalent flow rates and thus are not normally economically employed.

Flow rates of the gaseous feedstream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained. The hourly loading of the catalyst in a tube having a diameter of 22 mm and a length of 3 meters is generally from about 2000 to 6000 liters of air with about 20 to 150 g. of ortho-xylene per 1000 liters of air.

A variety of reactors will be found to be useful and multiple tube heat exchanger type reactors are quite satisfactory. The tubes of such reactors may vary in diameter typically from about 20 mm to 50 mm, and the length may be varied from about 1 to 5 meters.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon steel, nickel, glass tubes such as Vycor and the like. Both carbon steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the ortho-xylene concentration. Under usual operating conditions, in compliance with the preferred procedure of this invention, the average bed temperature referred to herein as the reaction temperature, measured by thermocouples disposed in the reactor, is typically from about 300° to about 500° C., preferably from about 320 to about 440° C., and most preferably from about 330° to about 420° C. Under normal conditions, the temperature in the reactor ordinarily should not be allowed to go above about 525° C. for extended lengths of time because of decreased yields and possible deactivation of the novel catalyst of this invention.

The reaction may be conducted at atmospheric, superatmospheric or below atmospheric pressure, with pressure of from 1 to 20 psig being generally entirely suitable.

The phthalic anhydride may be recovered by a number of ways well known to those skilled in the art. For example, the recovery may be by direct condensation or by absorption in suitable media, with subsequent separation and purification of the phthalic anhydride. By-products such as tolualdehyde, phthalide, and maleic anhydride may also be formed, and can be separated from the phthalic anhydride by conventional means. If the desired purified phthalic anhydride can be reacted with an organic alcohol (such as an oxo-alcohol, e.g., isodecyl alcohol) to prepare phthalate esters which find use as plasticizers.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, the reactor used to test the catalyst is described as follows:

The reactor tube for the catalyst bed was fabricated from 316 stainless steel and had a ⅜-inch outside diameter, a wall thickness of 0.049 inch and a length of 12 inches. The bottom of the reactor tube was charged with 2 cc of 3 mm glass beads (VICOR ® beads), and then about 2 g. of unsupported catalyst, having an average particle size of about 0.5 mm and premixed with about 15 g (8 ml) of 0.55 mm glass beads (VICOR ® beads), was charged to the reactor as the catalyst bed. On top of the catalyst bed was then placed 2 cc of 3 mm glass beads (VICOR ® beads). A ⅛-inch stainless steel thermowell tube was provided down the center of the reactor tube, and a thermocouple was provided within the thermowell for measurement of catalyst bed temperatures along the length of the reactor. The reactor tube was immersed in a HITEC ® salt bath. The reactor inlet pressure was about 1 psig. The o-xylene feed was caused to pass through the reactor tube in an upflow manner. Once a catalyst evaluation was started, the reaction was continued for the longer of the selected run time or 8 hours. At the conclusion of each run, the catalyst, if to be used again, was kept under nitrogen purge at a temperature of from about 320° to 330° C. Analyses of reactor effluent gas were made at convenient time intervals by gas chromatography. Carbon balance was calculated according to the number of gram atoms of carbon in the reactor effluent to the gram atoms of carbon fed to the system.

Conversion of ortho-xylene is calculated according the following equation:

$$\% \text{ o-xylene conversion} = \frac{\text{g-moles of reacted o-xylene}}{\text{g-moles of oxylene fed}} \times 100$$

Phthalic anhydride yield is calculated according to the following equation:

$$\% \text{ PAN yield} = \frac{\text{g-moles of PAN produced}}{\text{g-moles of o-xylene fed}} \times 100$$

The selectivity of phthalic anhydride is calculated according the the following equation:

$$\% \text{ selectivity to PAN} = \frac{\text{g-moles of PAN produced}}{\text{g-moles of o-xylene reacted}} \times 100$$

(% selectivity to intermediate oxidation products (e.g., tolualdehyde, phthalide) is calculated as shown above.)

In the Examples, the $TiO_2$ (Mobay) anatase charged was determined by atomic absorption analysis to contain about 0.15 wt % K, 0.10 wt % P, 0.10 wt % Al and 0.16 wt % Si (calculated as the respective elements) all of which are believed to be present as the corresponding metal oxides in the calcined catalysts prepared as described below. All Examples used $TiO_2$ (Mobay), 100% anatase, specific surface area of 9 m²/gm, pore size of 150–250 μm; −60+ −200 mesh. All amounts are weight % unless otherwise indicated.

EXAMPLES

Example 1: Catalyst Preparation

Comparative Catalyst A; 7.0% $V_2O_5$ on $ZrO_2$

To 70 ml of water is added 1.51 grams of vanadium pentoxide, 3.32 grams of oxalic acid and 7.53 grams of formamide at room temperature with stirring to form vanadium oxalate. This solution was then mixed with 20.0 grams of the zirconium dioxide powder (which were first dispersed in 20 ml of water). The resulting mixture was heated with stirring at 65° C. to concentrate the mixture by evaporating the majority of the water, followed by drying in an oven (101 kPa) at 110°

C. for 16 hours. The resulting solid was then calcined in a flowing oxygen gas stream at 450° C. for 2 hours, followed by crushing and screening to form −20+40 mesh particle size. The catalyst formed by the above impregnation procedure was determined by calculation (based on the vanadium salt and the weight of the zirconium dioxide particles) to contain 7.0 wt. % $V_2O_5$ on the $ZrO_2$.

Comparative Catalyst B-Sequential Deposition Catalyst; 7.0% $V_2O_5$/2.8% $TiO_2$ on $ZrO_2$ To 13.2 ml of toluene is added 2.55 grams of 95% titanium isopropoxide (containing an equivalent of 0.68 grams of $TiO_2$). This solution is then impregnated on 22 grams of $ZrO_2$ powder. The resulting mixture was dried in nitrogen at 120° C. for 5 hours and further heated in nitrogen at 500° C. for another hour to evaporate the toluene solvent. The resulting solids were then calcined in a flowing oxygen gas stream at 500° C. for 16 hours. A 22.4 gram portion of the resulting calcined powder was then impregnated with 70 ml of an aqueous solution containing 1.69 gram of $V_2O_5$, 3.71 grams of oxalic acid, and 8.43 grams of formamide, followed by concentration at 65° C. in air, drying in oven at 110° C. and calcining in a flowing oxygen atmosphere at 450° C. for 2 hours, as described above for preparation of catalyst A. The resulting solids were crushed into −20+40 mesh particles. The thus-formed catalyst was determined by calculation (based on the quantity of vanadium and titanium so impregnated thereon) to comprise 7.0 wt. % $V_2O_5$ and 2.8 wt. % $TiO_2$ on $ZrO_2$.

The zirconium dioxide powders used in preparation of Comparative Catalysts A and B were $ZrO_2$ (Baddelyite; Magnesium Elektron, Inc.), 7 m²/gm micron particles.

Catalyst C-Sequential Deposition Catalyst; 7.0% $V_2O_5$/4.3% $ZrO_2$ on $TiO_2$ To 17 ml of dry isopropanol was added 6.51 grams of zirconium n-propoxide (containing an equivalent of 2.45 grams of $ZrO_2$) and this solution was then impregnated on 50 grams of $TiO_2$ anatase powder. The resulting mixture was dried in air for 16 hours at room temperature and further dried in air at 100° C. for 16 hours. The resulting solid was then calcined in a flowing oxygen gas stream at 500° C. for 4 hours. A 19.2 gram portion of the resulting calcined powder was then impregnated with 70 m of an aqueous solution containing 1.44 grams of $V_2O_5$, 3.22 grams of oxalic acid, and 7.22 grams of formamide, followed by concentration at 65° C. in air, drying in oven at 110° C. and calcining in a flowing oxygen atmosphere at 450° C. for 2 hours, as described above for preparation of catalyst A. The resulting solids were crushed into −20+40 mesh particles. The thus-formed catalyst was determined by calculation (based on the quantity of vanadium and zirconium so impregnated thereon) to comprise 7.0 wt. % $V_2O_5$ and 4.3 wt. % $ZrO_2$ on $TiO_2$.

EXAMPLE 2—Preparation of Phthalic Anhydride

Employing the reactor and process conditions indicated, the catalyst prepared as above were charged to the reactor tube in separate runs to determine their activity for the partial oxidation of ortho-xylene to phthalic anhydride. The data thereby obtained are set forth in Table I below. These data are also indicated on the plot of FIGS. 1 and 2.

TABLE I

| Catalyst | Temp. (°C.) | Run[1] Time (hrs) | Conversion (mole %) | PAN Yield (mole %) | PAN Yield (wt. %) | Selectivities[2] (mole %) to | | |
|---|---|---|---|---|---|---|---|---|
| | | | | | | PAN | Tol | Ph |
| A (Comparative) | | | | | | | | |
| 7% $V_2O_5$/$ZrO_2$ | 353 | 3.0 | 87.3 | 48.2 | 67.2 | 55.2 | 2.9 | 3.9 |
| | 358 | 6.0 | 100.0 | 55.6 | 77.6 | 55.6 | 0.5 | 0.0 |
| | 351 | 3.1 | 83.4 | 47.9 | 66.8 | 57.4 | 2.8 | 3.3 |
| | 346 | 2.6 | 69.8 | 36.9 | 51.5 | 52.9 | 4.7 | 5.6 |
| | 343 | 2.5 | 61.8 | 31.2 | 43.5 | 50.5 | 5.7 | 7.0 |
| B (Comparative) | | | | | | | | |
| 7% $V_2O_5$/2.8% $TiO_2$ on $ZrO_2$ | 341 | 2.5 | 68.9 | 36.4 | 50.8 | 52.9 | 5.3 | 7.6 |
| | 335 | 2.5 | 55.1 | 26.4 | 36.9 | 48.0 | 7.6 | 9.6 |
| | 349 | 2.4 | 99.9 | 59.8 | 83.5 | 59.9 | 0.4 | 0.0 |
| | 346 | 3.0 | 90.2 | 54.0 | 75.4 | 59.9 | 1.8 | 2.5 |
| | 348 | 2.8 | 96.8 | 57.3 | 79.9 | 59.2 | 1.0 | 1.5 |
| C | | | | | | | | |
| 7% $V_2O_5$/4.3% $ZrO_2$ on $TiO_2$ (anatase) | 342 | 8.0 | 92.5 | 62.3 | 86.8 | 67.3 | 1.4 | 0.0 |
| | 336 | 3.2 | 74.7 | 50.5 | 70.4 | 67.6 | 3.6 | 2.0 |
| | 331 | 2.3 | 56.6 | 35.9 | 50.1 | 63.5 | 6.5 | 3.6 |
| | 344 | 2.4 | 97.2 | 65.5 | 91.4 | 67.4 | 0.8 | 0.0 |

Notes:
"PAN" = phthalic anhydride;
"Tol" = tolualdehyde;
"Ph" = phthalide
[1]Vapor feed to reactor = 1.25 mol. % o-xylene in air; space velocity = 2760 hr.⁻¹
[2]Σ $C_8$ oxygenate selectivities of FIG. 1 = Σ selectivities to PAN, Tol and Ph.

Figure 2:
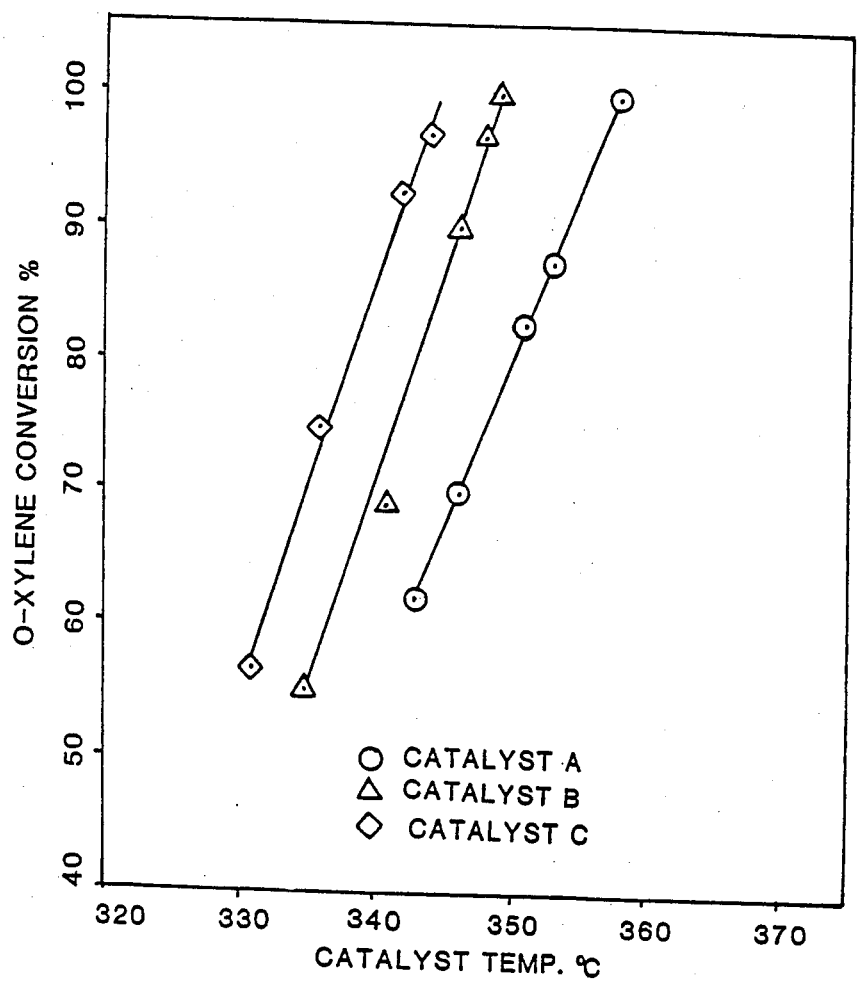
FIG. 2 is a graphical plot of o-xylene conversion versus temperature, as obtained in Examples 1–2.

From the data in Table I, and FIGS. 1 and 2, it can be seen that Comparative Catalyst A (7% $V_2O_5$ on $ZrO_2$) was only able to achieve a phthalic anhydride selectivity of about 58 mol. % at 97 mol. % o-xylene conversion, and Comparative Catalyst B (7% $V_2O_5$ on a surface modified $ZrO_2$ having 2.8% $TiO_2$ thereon) gave phthalic anhydride selectivities of only about 59 mol. % at an o-xylene conversion of about 97 mol. %. In contrast, Catalyst C of this invention gave a phthalic anhydride selectivity of about 67.4% at about 97 mol. % o-xylene conversion, and the PAN selectivity remained higher than the PAN selectivities of Comparative Catalysts A and B over the entire o-xylene conversion range of 65–100 mol%.

From FIG. 2, it can be seen that the Catalyst C of this invention exhibits a higher activity for o-xylene conversion than Comparative Catalysts A and B, at all tested temperatures. For example, an o-xylene conversion of 95 mol. % was achieved at about 343° C. for Catalyst C of this invention, whereas Comparative Catalysts A and B required temperatures of about 355° C. and 346° C., respectively, to achieve this level of o-xylene conversion.

It will be obvious that various changes and modifications may be made without departure from the invention, and it is intended, therefore, that all matter contained in the foregoing description shall be interpreted as illustrative only and not limitative of the invention.

What is claimed is:

1. A process for preparing a catalyst composition comprising vanadium, zirconium and oxygen capable of catalyzing the oxidation of hydrocarbons which comprises:
    (a) contacting titanium dioxide with a zirconium oxide source in a manner and under conditions sufficient to apply a continuous monolayer amount of said zirconium oxide source on said titanium dioxide to form a catalyst precursor;
    (b) calcining said catalyst precursor in a manner and under conditions sufficient to convert at least a portion of said zirconium oxide source to zirconium dioxide, to form a calcined catalyst precursor having a continuous monolayer amount of zirconium dioxide adsorbed on said titanium dioxide;
    (c) depositing a catalytically effective amount of at least one vanadium oxide source on said calcined catalyst precursor, to form a vanadium-containing catalyst precursor; and
    (d) calcining said vanadium-containing catalyst precursor in a manner and under conditions sufficient to convert said vanadium oxide source to vanadium oxide, thereby forming said catalyst composition which comprises from about 0.7 to 50 wt. % of vanadium oxides, calculated as $V_2O_5$ and wherein the mole ratio of vanadium to zirconium is about 0.1:1 to 20,000:1.

2. The process according to claim 1 wherein said catalyst precursor is calcined in step (b) at a temperature of from about 100° to 750° C.

3. The process according to claim 2 wherein said calcining is effected for a time of from about 0.5 to 16 hours.

4. The process according to claim 1 wherein said zirconium source comprises at least one member selected from the group consisting of zirconium halides, phosphates, oxides, carbonates, sulfates, alkoxides, nitrates, hydroxides, carboxylates and oxy halides.

5. The process according to claim 1 wherein said zirconium source comprises at least one member selected from the group consisting of zirconium chloride, zirconium phosphate, zirconium nitride, zirconium carbonate, zirconium sulfate, zirconium nitrate, zirconium oxalate, zirconium hydroxide, zirconium acetate, zirconium tartrate and zirconium oxychloride.

6. The process according to claim 1 wherein said vanadium source comprises at least one compound selected from the group consisting of vanadium pentoxide, ammonium metavanadate, vanadyl sulfate, vanadyl chloride, vanadyl dichloride, metavanadic acid, pyrovanatic acid, vanadium hydroxide, and vanadyl carboxylates.

7. The process according to claim 1 wherein said catalyst, following calcination according to step (d), is defined by a vanadium:Zr atomic ratio of from about 0.5:1 to 2,000:1.

8. The process according to claim 1 wherein said catalyst, following calcination according to step (d), is characterized by specific surface area of less than 50 square meters per gram.

9. The process according to claim 1 wherein said vanadium oxide source in step (c) is deposited upon said calcined catalyst precursor in an amount sufficient to provide at least $N_{min}$ grams of $V_2O_5$, wherein $$N_{min} = (G) \times (A) \times (0.0007)$$

wherein "G" is the grams of said calcined catalyst precursor and "A" is the specific surface area of said titanium dioxide.

10. The process according to claim 6 wherein said vanadyl carboxylate compound comprises at least one compound selected from vanadyl formate, vanadyl tartrate, vanadyl salicylate and vanadyl oxalate.

* * * * *